United States Patent [19]

Berner et al.

[11] 4,419,472

[45] Dec. 6, 1983

[54] PIPERIDINE COMPOSITIONS FOR LIGHT STABILIZATION

[75] Inventors: Godwin Berner, Rheinfelden; Manfred Rembold, Basel; Jean Rody, Riehen, all of Switzerland

[73] Assignee: Ciba-Geigy Corporation, Ardsley, N.Y.

[21] Appl. No.: 322,041

[22] Filed: Nov. 16, 1981

[30] Foreign Application Priority Data

Nov. 17, 1980 [CH] Switzerland ............... 8520/80

[51] Int. Cl.³ .............. C08K 5/34; C07D 401/12; C07D 401/06
[52] U.S. Cl. .............. 524/102; 546/188; 546/222; 546/242
[58] Field of Search .............. 546/188, 222, 242; 524/102

[56] References Cited

U.S. PATENT DOCUMENTS

| | | | |
|---|---|---|---|
| 4,021,432 | 5/1977 | Holt et al. | 346/188 |
| 4,141,883 | 2/1979 | Soma et al. | 546/16 |
| 4,238,613 | 12/1980 | Rasberger et al. | 546/190 |

*Primary Examiner*—Robert T. Bond
*Attorney, Agent, or Firm*—Luther A. R. Hall

[57] ABSTRACT

The invention relates to ester mixtures of polyalkylpiperidine derivatives of the formulae I and II

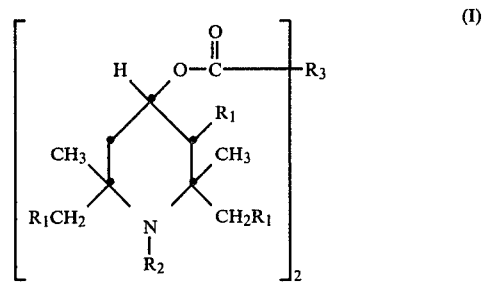

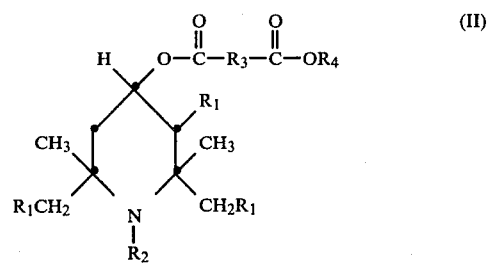

in which $R_1$ is hydrogen or methyl, $R_2$ is hydrogen, $C_{1-12}$ alkyl, $C_{3-8}$ alkenyl, $C_{7-11}$ aralkyl, cyanomethyl or $C_{2-4}$ acyl, $R_3$ is $C_{1-18}$ alkylene, $C_{2-18}$ oxaalkylene, Chd 2-18 thiaalkylene, $C_{2-18}$ azaalkylene or $C_{2-8}$ alkenylene and $R_4$ is $C_{1-4}$ alkyl. These mixtures are suitable as stabilizers for plastics.

9 Claims, No Drawings

PIPERIDINE COMPOSITIONS FOR LIGHT STABILIZATION

The invention relates to novel ester mixtures of polyalkylpiperidine derivatives, their preparation and their use as stabilisers for plastics and to the material stabilised therewith.

Polyalkylpiperidine esters, such as bis-(1,2,2,6,6-pentamethyl-4-piperidyl) sebacate, have been disclosed as light stabilisers for plastics in U.S. Pat. No. 4,021,432, For practical application, known stabilisers of this type have not always proved satisfactory. Especially when solid substances are used, where necessary also in the form of solutions, disadvantages arise in practice which lead to problems, for example in the preparation of lacquers which are stable to light, such as automotive lacquers. For this reason, the known light stabilisers are not suitable for use in lacquer systems with a low solvent content (high solids).

It is the object of the present invention to provide novel light stabilisers which do not have these disadvantages, or which have them to a considerably lesser extent, and which, in particular, are readily compatible with the substrate, can be incorporated easily in the substrate and disperse rapidly and homogeneously, such that the substrate is provided with effective and long-lasting protection against the harmful influence of light.

Accordingly, the invention relates to ester mixtures of polyalkylpiperidine derivatives of the formulae I and II

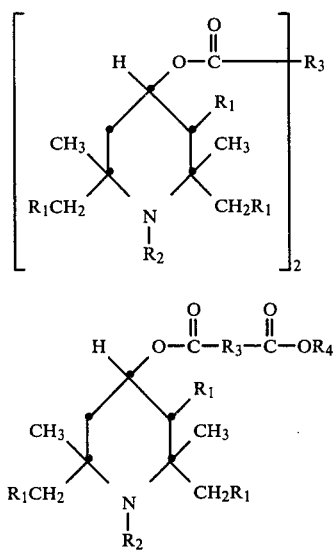

in which $R_1$ is hydrogen or methyl, $R_2$ is hydrogen, $C_{1-12}$ alkyl, $C_{3-8}$ alkenyl, $C_{7-11}$ aralkyl, cyanomethyl or $C_{2-4}$ acyl, $R_3$ is $C_{1-18}$ alkylene, $C_2-C_{18}$ oxaalkylene, $C_{2-18}$ thiaalkylene, $C_{2-18}$ azaalkylene or $C_{2-8}$ alkenylene and $R_4$ is $C_{1-4}$ alkyl.

$R_2$ as $C_{1-12}$ alkyl is preferably straight chain alkyl with, in particular, 1–4 C atoms, such as ethyl, n-propyl, n-butyl and in particular methyl.

$R_2$ as $C_{3-8}$ alkenyl is preferably straight chain alkenyl, in particular allyl.

$R_2$ as $C_{7-11}$ aralkyl is preferably benzyl.

$R_2$ as $C_{2-4}$ acyl is preferably alkanoyl or alkenoyl, ausch as propionyl, acryloyl and, most preferably, acetyl.

$R_3$ as $C_{1-18}$ alkylene is branched or, preferably, straight chain alkylene, especially alkylene having 1–10 C atoms, such as methylene, ethylene, trimethylene, tetramethylene, hexamethylene, decamethylene and, most particularly, octamethylene.

$R_3$ as $C_{2-18}$ oxaalkylene is preferably straight chain oxaalkylene having, in particular, 2–9 C atoms, such as 2-oxa-trimethylene or 3-oxa-pentamethylene.

$R_3$ as $C_{2-18}$ thiaalkylene is preferably straight chain thiaalkylene having, in particular, 2–9 C atoms, such as 2-thia-trimethylene or 3-thia-pentamethylene.

$R_3$ as $C_{2-18}$ azaalkylene is azaalkylene which is straight chain or branched, especially branched at the aza, and has, in particular, 2–9 C atoms, such as 3-aza-pentamethylene, 3-aza-3-methyl-pentamethylene, 4-aza-heptamethylene or 4-aza-4-methyl-heptamethylene.

$R_3$ as $C_{2-8}$ alkenylene is preferably straight chain alkenylene, such as ethenylene or 2-buten-1,4-ylene.

$R_4$ as $C_{1-4}$ alkyl is, for example, ethyl, n-propyl, i-propyl, n-butyl, i-butyl or, preferably, methyl.

Preferred mixtures of esters of the formulae I and II are those in which $R_1$ is hydrogen, $R_2$ is $C_{1-4}$ alkyl or benzyl, $R_3$ is $C_{1-18}$ alkylene and $R_4$ is $C_{1-4}$ alkyl.

Particularly preferred mixtures of esters of the formulae I and II are those in which $R_1$ is hydrogen, $R_2$ is methyl or benzyl, $R_3$ is straight chain $C_{2-10}$ alkylene and $R_4$ is $C_{1-4}$ alkyl.

The most preferred mixtures of esters of the formulae I and II are those in which $R_1$ is hydrogen, $R_2$ is methyl, $R_3$ is octamethylene and $R_4$ is methyl.

The ratio of the esters I and II can vary within wide limits. However, those ester mixtures containing 98–60% by weight of I and 2–40% by weight of II, and in particular 90–70% by weight of I and 10–30% by weight of II, are preferred.

The ester mixtures according to the invention can be prepared by methods known per se, for example by reacting a piperidine of the formula III with a diester of the formula IV

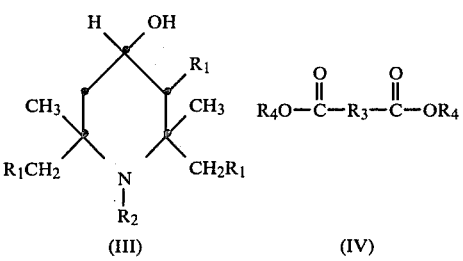

in which formulae $R_1$, $R_2$, $R_3$ and $R_4$ are as defined. The procedure employed for the reaction is preferably that customary for transesterifications, such that about 1.01 to 1.5 moles of IV preferably are used per 2 moles of III. However, it is also possible, if desired, to prepare components I and II separately by methods known per se, to purify these components if desired and then to mix components I and II.

The starting materials are known. Any that may still be novel can be prepared by methods similar to those for preparing known starting materials.

According to the present invention, the mixtures of esters of the formulae I and II can be used as stabilisers to protect plastics against damage caused by the action of oxygen, heat and, in particular, light. Examples of such plastics are:

1. Polymers of mono- and diolefins, for example polyethylene (which can be crosslinked), polypropylene, polyisobutylene, polybut-1-ene, polymethylpent-1-ene, polyisoprene or polybutadiene, and polymers of cycloolefins, e.g. of cyclopentene or norbornene.

2. Mixtures of the polymers mentioned under (1), for example mixtures of polypropylene with polyethylene or with polyisobutylene.

3. Copolymers of mono- and diolefins with each other or with other vinyl monomers, for example ethylene/propylene copolymers, propylene/but-1-ene copolymers, propylene/isobutylene copolymers, ethylene/but-1-ene copolymers, propylene/butadiene copolymers, isobutylene/isoprene copolymers, ethylene/alkylacrylate copolymers, ethylene/alkylmethacrylate copolymers, ethylene/vinyl acetate copolymers, or ethylene/acrylic acid copolymers and salts thereof (ionomers), and also terpolymers of ethylene with propylene and a diene, such as hexadiene, dicyclopentadiene or ethylidenenorbornene.

4. Polystyrene.

5. Copolymers of styrene or α-methylstyrene with dienes or acrylic derivatives, for example styrene/butadiene, styrene/acrylonitrile, styrene/alkylmethacrylate, styrene/acrylonitrile/methyl acrylate; mixtures of high impact strength obtained from styrene copolymers and another polymer, for example a polyacrylate, a diene polymer or an ethylene/propylene/diene terpolymer; and also block copolymers of styrene, for example styrene/butadiene/styrene, styrene/isoprene/styrene, styrene/ethylene-butylene/styrene, or styrene-ethylene/propylene-styrene.

6. Graft copolymers of styrene, e.g. styrene with polybutadiene, styrene and acrylonitrile with polybutadiene, styrene and maleic anhydride with polybutadiene, styrene and alkyl acrylates or alkyl methacrylates with polybutadiene, styrene and acrylonitrile with ethylene-propylene-diene terpolymers, styrene and acrylonitrile with polyalkylacrylates or polyalkylmethacrylates, styrene and acrylonitrile with acrylate-butadiene copolymers, and mixtures thereof with the copolymers listed under (5), known e.g. as ABS, MBS, ASA or AES polymers.

(7) Halogen-containing polymers, e.g. polychloroprene, chlorinated rubber, chlorinated or chlorosulfonated polyethylene, especially polymers of halogenated vinyl compounds, e.g. polyvinyl chloride, polyvinylidene chloride, polyvinyl fluoride, polyvinylidene fluoride, and their copolymers such as vinyl chloride/vinylidene chloride, vinyl chloride/vinyl acetate or vinylidene chloride/vinyl acetate.

8. Polymers which are derived from α,β-unsaturated acids and their derivatives, such as polyacrylates and polymethacrylates, polyacrylamides and polyacrylonitriles.

9. Copolymers of the monomers listed in (8) with one another or with other unsaturated monomers, e.g. acrylonitrile/butadiene copolymers, acrylonitrile/alkyl acrylate copolymers, acrylonitrile/vinyl chloride copolymers, or acrylonitrile/alkyl methacrylate/butadiene terpolymers.

10. Polymers which are derived from unsaturated alcohols and amines or their acyl derivatives or acetals, such as polyvinyl alcohol, polyvinyl acetate, polyvinyl stearate, polyvinyl benzoate, polyvinyl maleate, polyvinylbutyral, polyallyl phthalate, polyallylmelamine.

11. Homopolymers and copolymers of cyclic ethers such as polyethylene glycols, polyethylene oxide, polypropylene oxide or their copolymers with bis-glycidyl ethers.

12. Polyacetals such as polyoxymethylene, and also those polyoxymethylenes which contain a comonomer, e.g. ethylene oxide.

13. Polyphenylene oxides and sulfides.

14. Polyurethanes which are derived on the one hand from polyethers, polyesters and polybutadienes containing hydroxy end groups, and from aliphatic or aromatic polyisocyanates on the other, as well as their precursors.

15. Polyamides and copolyamides which are derived from diamines and dicarboxylic acids and/or from aminocarboxylic acids or the corresponding lactams, such as polyamide 4, polyamide 6, polyamide 66, polyamide 610, polyamide 11, polyamide 12, poly-2,4,4-trimethylhexamethyleneterephthalamide, poly-m-phenylene-isophthalamide, and their copolymers with polyethers, e.g. with polyethylene glycol, polypropylene glycol or polytetramethylene glycol.

16. Polyureas, polyimides and polyamide imides.

17. Polyesters which are derived from decarboxylic acids and dialcohols and/or from hydroxycarboxylic acids or the corresponding lactones, such as polyethylene terephthalate, polybutylene terephthalate and poly-1,4-dimethylolcyclohexane terephthalate, and also block polyether esters which are derived from polyethers having hydroxyl end groups and dicarboxylic acids.

18. Polycarbonates.

19. Polysulfones and polyether sulfones.

20. Crosslinked polymers which are derived from aldehydes on the one hand and from phenols, ureas and melamines on the other hand, such as phenol-formaldehyde resins, urea-formaldehyde resins and melamine-formaldehyde resins.

21. Drying and non-drying alkyd resin.

22. Unsaturated polyester resins which are derived from copolyesters of saturated and unsaturated dicarboxylic acids with polyhydric alcohols and vinyl compounds as crosslinking agents, and also their halogen-containing modifications of low combustibility.

23. Crosslinkable acrylic resins which are derived from substituted acrylic esters, e.g. from epoxy acrylates, urethane acrylates or polyester acrylates.

24. Alkyd resins, polyester resins and acrylate resins which are crosslinked with melamine resins, urea resins, polyisocyanates or epoxy resins.

25. Crosslinked epoxy resins which are derived from polyepoxides, e.g. bis-glycidyl ethers, or from cycloaliphatic diepoxides.

26. Naturally occurring polymers, such as cellulose, rubber and gelatin, and also their polymer-homologously chemically modified derivatives, such as cellulose acetates, cellulose propionates and cellulose butyrates, and cellulose ethers such as methylcellulose.

The stabilisation of lacquers is of particular importance.

The stabilisers are incorporated in the plastics in a concentration of 0.01 to 5% by weight, based on the material to be stabilised. Preferably, 0.03 to 1.5% by weight, most preferably 0.2 to 0.6% by weight, of the compounds, based on the material to be stabilised, are incorporated into the latter.

Incorporation can be effected after polymerisation, for example by blending the compounds and, if desired, further additives, into the melt by methods conventionally employed in the art, before or during shaping, or also by applying the dissolved or dispersed compounds to the polymer, with subsequent evaporation of the solvent if necessary.

The novel mixtures can also be added in the form of a master batch which contains these compounds, for example in a concentration of 2.5 to 25% by weight, to the plastics to be stabilised.

If crosslinked polyethylene is used, the compounds are added prior to crosslinking.

In addition to the mixtures of the esters of the formulae I and II, yet further known stabilisers and co-stabilisers can also be incorporated in the plastics. These stabilisers can be, for example:

1. Antioxidants 1.1. Alkylated monophenols
2,6-Di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-i-butylphenol, 2,6-di-cyclopentyl-4-methylphenol, 2-($\alpha$-methylcyclohexyl)-4,6-dimethylphenol, 2,6-di-octadecyl-4-methylphenol or 2,4,6-tri-cyclohexylphenol.

1.2. Alkylated hydroquinones
2,6-Di-tert-butyl-4-methoxyphenol, 2,5-di-tert-butylhydroquinone or 2,5-di-tert-amyl-hydroquinone.

1.3. Hydroxylated thiophenyl ethers
2,2'-Thio-bis-(6-tert-butyl-4-methylphenol), 2,2'-thio-bis-(4-octylphenol), 4,4'-thio-bis-(6-tert-butyl-3-methylphenol) or 4,4'-thio-bis-(6-tert-butyl-2-methylphenol).

1.4. Alkylidene-bisphenols
2,2'-Methylene-bis-(6-tert-butyl-4-methylphenol), 2,2'-methylene-bis-(6-tert-butyl-4-ethylphenol), 2,2'-methylene-bis-[4-methyl-6-($\alpha$-methylcyclohexyl)-phenol], 2,2'-methylene-bis-(4-methyl-6-cyclohexylphenol), 2,2'-methylene-bis-(6-nonyl-4-methylphenol), 2,2'-methylene-bis-(4,6-di-tert-butylphenol), 2,2'-ethylidene-bis-4,6-di-tert-butylphenol), 2,2'-ethylidene-bis-(6-tert-butyl-4-isobutylphenol), 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenyl)-butane, 2,6-di-(3-tert-butyl-5-methyl-2-hydroxybenzyl)-4-methylphenol, 1,1,3-tris-(5-tert-butyl-4-hydroxy-2-methylphenyl)-butane, 1,1-bis-(5-tert-butyl-4-hydroxy-2-methylphenyl)-3-n-dodecylmercaptobutane, ethylene glycol bis-[3,3-bis-(3'-tert-butyl-4'-hydroxyphenyl)-butyrate], di-(3-tert-butyl-4-hydroxy-5-methylphenyl)-dicyclopentadiene or di-[2-(3'-tert-butyl-2'-hydroxy-5':methyl-benzyl)-6-tert-butyl-4-methyl-phenyl]terephthalate.

1.5. Benzyl compounds
1,3,5-Tri-(3,5-di-tert-butyl-4-hydroxybenzyl)-2,4,6-trimethylbenzene, di-(3,5-di-tert-butyl-4-hydroxybenzyl) sulfide, isooctyl 3,5-di-tert-butyl-4-hydroxybenzyl-mercaptoacetate, bis-(4-tert-butyl-3-hydroxy-2,6-dimethylbenzyl)-dithiol terephthalate, 1,3,5-tris-(3,5-di-tert-butyl-4-hydroxybenzyl)isocyanurate, 1,3,5-tris-(4-tert-butyl-3-hydroxy-2,6-dimethylbenzyl)isocyanurate, di-octadecyl 3,5-di-tert-butyl-4-hydroxyphenyl-phosphonate or the calcium salt of monoethyl 3,5-di-tert-butyl-4-hydroxybenzyl-phosphonate.

1.6. Acylaminophenols
4-Hydroxy-lauric acid anilide, 4-hydroxy-stearic acid anilide or 2,4-bis-octylmercapto-6-(3,5-di-tert-butyl-4-hydroxyanilino)-S-triazine.

1.7. Esters of $\beta$-(3,5-di-tert-butyl-4-hydroxyphenyl)-propionic acid with monohydric or polyhydric alcohols, for example with methanol, octadecanol, 1,6-hexanediol, neopentylglycol, thiodiethylene glycol, diethylene glycol, triethylene glycol, pentaerythritol, trishydroxyethyl isocyanurate or di-hydroxyethyl-oxalamide.

1.8. Esters of $\beta$-(5-tert-butyl-4-hydroxy-3-methylphenyl)-propionic acid with monohydric or polyhydric alcohols, for example with methanol, octadecanol, 1,6-hexanediol, neopentylglycol, thiodiethylene glycol, diethylene glycol, triethylene glycol, pentaerythritol, tris-hydroxyethyl isocyanurate or di-hydroxyethyl-oxalamide.

1.9. Amides of $\beta$-(3,5-di-tert-butyl-4-hydroxyphenyl)-propionic acid, for example N,N'-di-(3,5-di-tert-butyl-4-hydroxyphenylpropionyl)-hexamethylenediamine, N,N'-di-(3,5-di-tert-butyl-4-hydroxyphenylpropionyl)-trimethylenediamine or N,N'-di-(3,5-di-tert-butyl-4-hydroxyphenylpropionyl)-hydrazine.

2. UV-absorbers and light stabilisers 2.1. 2-(2'-Hydroxyphenyl)-benztriazoles, for example 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec.-butyl-5'-tert-butyl-, 4'-octoxy-, 3',5'-di-tert-amyl-, 3',5'-di-(1,1,3,3-tetramethylbutyl)- and 3',5'-di-($\alpha$,$\alpha$-dimethylbenzyl)-2-(2'-hydroxyphenyl)-benztriazole.

2.2. 2-Hydroxybenzophenones, for example the 4-hydroxy-, 4-methoxy-, 4-octoxy-, 4-decyloxy-, 4-dodecyloxy-, 4-benzyloxy-, 4,2',4'-trihydroxy- and 2'-hydroxy-4,4'-dimethoxy-derivatives.

2.3. Esters of substituted and unsubstituted benzoic acids, for example 4-tert-butyl-phenyl salicylate, phenyl salicylate, octylphenyl salicylate, dibenzoylresorcinol, bis-(4-tert-butylbenzoyl)-resorcinol, benzoylresorcinol and 2,4-di-tert-butyl-phenyl 3,5-di-tert-butyl-4-hydroxybenzoate.

2.4. Acrylates, for example ethyl $\alpha$-cyano-$\beta$,$\beta$-diphenylacrylate, isooctyl $\alpha$-cyano-$\beta$,$\beta$-diphenylacrylate, methyl $\alpha$-carbomethoxy-cinnamate, methyl $\alpha$-cyano-$\beta$-methyl-p-methoxy-cinnamate, butyl $\alpha$-cyano-$\beta$-methyl-p-methoxy-cinnamate, methyl $\alpha$-carbomethoxy-p-methoxy-cinnamate and N-($\beta$-carbomethoxy-$\beta$-cyanovinyl)-2-methyl-indoline.

2.5. Nickel compounds, for example nickel complexes of 2,2'-thio-bis-[4-(1,1,3,3-tetramethylbutyl)-phenol], such as the 1:1 complex or the 1:2 complex, if desired with additional ligands such as n-butylamine, triethanolamine or N-cyclohexyl-diethanolamine, nickel dibutyl-dithiocarbamate, nickel salts of 4-hydroxy-3,5-di-tert-butylbenzyl-phosphonic acid monoalkyl esters, such as of the methyl or ethyl ester, nickel complexes of ketoximes, such as of 2-hydroxy-4-methyl-phenyl undecyl ketone oxime, and nickel complexes of 1-phenyl-4-lauroyl-5-hydroxypyrazole, if desired with additional ligands.

2.6. Sterically hindered amines, for example bis-(2,2,6,6-tetramethylpiperidyl)sebacate, bis-(1,2,2,6,6pentamethylpiperidyl)sebacate, Bis-(1,2,2,6,6-pentamethylpiperidyl) n-butyl-3,5-di-tert-butyl-4-hydroxybenzylmalonate, the condensation product of 1-hydroxyethyl-2,2,6,6-tetramethyl-4-hydroxypiperidine and succinic acid, the condensation product of N,N'-(2,2,6,6-tetramethylpiperidyl)-hexamethylenediamine and 4-tert-octylamino-2,6-dichloro-1,3,5-s-triazine, and tris-(2,2,6,6-tetramethylpiperidyl)nitrilotriacetate.

2.7. Oxalic acid diamides, for example 4,4'-di-octyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis-(3-dimethylaminopropyl)-oxalamide, 2-ethoxy-5-tert-butyl-2'-ethyl-oxanilide and its mixture with 2-ethoxy-2'-ethyl-5,4'-di-tert-butyl-oxanilide, mixtures of ortho- and paramethoxy-disubstituted oxanilides and mixtures of o- and p-ethoxy-disubstituted oxanilides.

3. Metal deactivators, for example N,N'-diphenyloxalic acid diamide, N-salicylal-N'-salicyloylhydrazine, N,N'-bis-salicyloylhydrazine, N,N'-bis-(3,5.1-di-tert-butyl-4-hydroxyphenylpropionyl)-hydrazine, 3-salicyloylamino-1,2,4-triazole and bis-benzylidene-oxalic acid dihydrazide.

4. Phosphites and phosphonites, for example triphenyl phosphite, diphenyl alkyl phosphites, phenyl dialkyl phosphites, tri(nonylphenyl)phosphite, trilauryl phosphite, trioctadecyl phosphite, distearyl-pentaerythritol diphosphite, tris-(2,4-di-tert-butylphenyl)phosphite, diisodecyl-pentaerythritol diphosphite, di-(2,4-di-tert-butylphenyl)-pentaerythritol diphosphite, tristearylsorbitol triphosphite and tetrakis-(2,4-di-tert-butylphenyl)-4,4'-biphenylene diphosphonite.

5. Compounds which decompose peroxide, for example esters of β-thio-dipropionic acid, for example the lauryl, stearyl, myristyl or tridecyl ester, mercaptobenzimidazole, the zinc salt of 2-mercaptobenzimidazole, zinc dibutyldithiocarbamate, dioctadecyl disulfide and pentaerythritol tetrakis-(β-dodecylmercapto)propionate.

6. Polyamide stabilisers, for example copper salts in combination with iodides and/or phosphorous compounds and salts of divalent manganese.

7. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium stearate, sodium ricinoleate and potassium palmitate, antimony pyrocatechoate or tin pyrocatechoate.

8. Nucleating agents, for example 4-tert-butylbenzoic acid, adipic acid and diphenylacetic acid.

9. Fillers and reinforcing agents, for example calcium carbonates, silicates, glass fibres, asbestos, talc, kaolin, mica, barium sulfate, metal oxides and metal hydroxides, carbon black and graphite.

10. Other additives, for example plasticisers, lubricants, emulsifiers, pigments, fluorescent whitening agents, flameproofing agents, antistatic agents and blowing agents.

Known and conventional additives of this type are not only compatible with the mixtures of esters of the formulae I and II but, in individual cases, can also result in a synergistic potentiation.

The invention therefore also relates to plastics which have been stabilised by the addition of 0.01 to 5% by weight of a mixture of esters of the formula I and II, and which, if desired, can contain yet further known and conventional additives. The plastics so stabilised can be used in very diverse forms, for example as films, fibres, ribbons, profiles or sheets or as injection-moulded articles. They can also be used in foamed form. Furthermore, they can also be used as binders for lacquers, adhesives or putties and also as coating materials and base materials in photographic materials.

The following Examples illustrate the invention, but imply no restriction to what is described therein.

EXAMPLE 1

230.3 g (1 mole) of dimethyl sebacate and 308.3 g (1.8 moles) of 1,2,2,6,6-pentamethyl-4-hydroxy-piperidine are heated with 120 ml of xylene to about 135° C., under a weak flow of nitrogen. To effect total dehydration of the mixture, about 20 ml of xylene are distilled off. Then 1 g of tetrabutyl orthotitanate is added to the reaction mixture, which is heated to 130°–40° C. under a weak flow of nitrogen. Regular distillation of methanol/xylene very soon starts. The internal temperature is raised to 160° C. over 3–4 hours and the contents of the flask are further stirred at this temperature until, after about 10 hours, virtually nothing more distils over. The final traces of solvent are removed by distillation under a high vacuum at about 110° C./0.001 torr, and the residue in the flask is clarified through a glass frit. The resultant, slightly yellowish, oily liquid is a mixture consisting of about 85% of bis-(1,2,2,6,6-pentamethyl-4-piperidinyl)sebacate and about 15% of mono-(1,2,2,6,6-pentamethyl-4-piperidinyl)monomethyl sebacate.

EXAMPLE 2

Crystallisation tendency of the ester mixtures of the invention

The crystallisation tendency of the ester mixtures of the invention is dependent on the mixture ratio of the components I and II. Depending on the utility, small amounts of component II suffice. If, however, a stable, fluid ester mixture is desired, the amount of component II can be slightly increased.

Bis-(1,2,2,6,6-pentamethyl-4-piperidinyl)sebacate is used as component I and mono-(1,2,2,6,6-pentamethyl-4-piperidinyl)monomethyl-sebacate is used as component II.

The ester mixtures are stored at 0° C. and −20° C. and the time is measured until they crystallise completely. Longer times mean an increase in stability of the fluid consistency of the ester mixtures.

| Amount of component II | Days until complete crystallisation at | |
|---|---|---|
| | 0° C. | −20° C. |
| 0% | 0 | 0 |
| 6% | 2–5 | 1–2 |
| 10% | 27–35 | |
| 17% | >90 | 15–20 |
| 20% | >90 | 25–30 |
| 24% | >90 | 60–70 |
| 65% | | >150 |

Surprisingly, it requires an extremely large and undesirable addition of solvent to attain similarly satisfactory results.

What is claimed is:

1. A composition, which is a mixture of esters of the formulae I and II, which comprises
    (a) 90–70% by weight of an ester of formula I

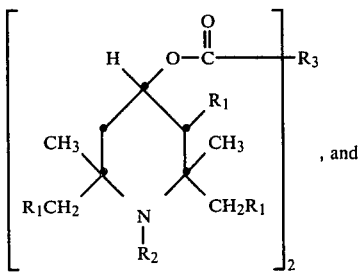

(b) 10–30% by weight of an ester of formula II

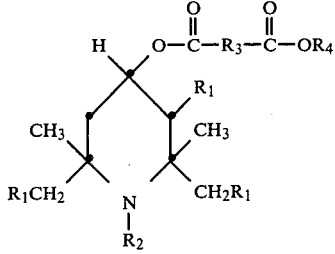

in which $R_1$ is hydrogen or methyl, $R_2$ is hydrogen, $C_{1-12}$ alkyl, $C_{3-8}$ alkenyl, $C_{7-11}$ aralkyl, cyanomethyl or $C_{2-4}$ acyl, $R_3$ is $C_{1-18}$ alkylene, $C_2$-$C_{18}$ oxaalkylene, $C_{2-18}$ thiaalkylene, $C_{2-18}$ azaalkylene or $C_{2-8}$ alkenylene and $R_4$ is $C_{1-4}$ alkyl.

2. A composition according to claim 1, in which $R_1$ is hydrogen, $R_2$ is $C_{1-4}$ alkyl or benzyl, $R_2$ is $C_{1-18}$ alkylene and $R_4$ is $C_{1-4}$ alkyl.

3. A composition according to claim 1, in which $R_1$ is hydrogen, $R_2$ is methyl or benzyl, $R_3$ is straight chain $C_{2-10}$ alkylene and $R_4$ is $C_{1-4}$ alkyl.

4. A composition according to claim 1, in which $R_1$ is hydrogen, $R_2$ is methyl, $R_3$ is octamethylene and $R_4$ is methyl.

5. A composition according to claim 1, wherein the compound of formula I is bis-(1,2,2,6,6-pentamethyl-4-piperidinyl)sebacate and the compound of formula II is mono-(1,2,2,6,6-pentamethyl-4-piperidinyl)-monomethyl sebacate.

6. A process for the preparation of a composition according to claim 1, which process comprises reacting a piperidine of the formula III with a diester of the formula IV

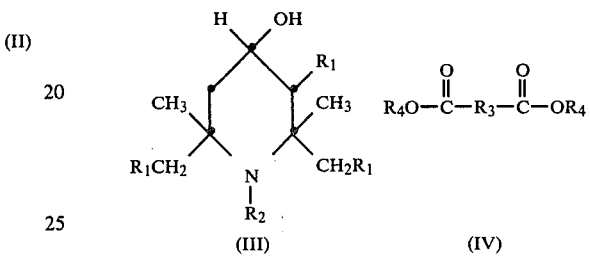

in which formulae $R_1$, $R_2$, $R_3$ and $R_4$ have the given meanings.

7. A process for stabilising plastics material against photochemical degradation, by the addition of 0.01 to 5% by weight of a composition according to claim 1.

8. Plastics material which has been stabilised against photochemical degradation and which contains, as stabiliser, 0,1 to 5% by weight of a composition according to claim 1.

9. Stabilised plastics material according to claim 8, which is a lacquer.

* * * * *